(12) United States Patent
Mello et al.

(10) Patent No.: US 8,932,456 B2
(45) Date of Patent: Jan. 13, 2015

(54) INTEGRATED PROCESS FOR THE MANUFACTURE OF OLEFINS AND INTERMEDIATES FOR THE PRODUCTIONS OF AMMONIA AND UREA

(75) Inventors: Leonardo Fialho de Mello, Rio de Janeiro (BR); Oscar Rene Chamberlain Pravia, Rio de Janeiro (BR); Gustavo Torres Moure, Rio de Janeiro (BR)

(73) Assignee: Petroleo Brasileiro S.A.—Petrobras, Rio de Janeiro (BR)

( * ) Notice: Subject to any disclaimer, the term of this patent is extended or adjusted under 35 U.S.C. 154(b) by 831 days.

(21) Appl. No.: 13/139,892

(22) PCT Filed: Oct. 21, 2009

(86) PCT No.: PCT/BR2009/000343
§ 371 (c)(1),
(2), (4) Date: Jun. 15, 2011

(87) PCT Pub. No.: WO2010/069018
PCT Pub. Date: Jun. 24, 2010

(65) Prior Publication Data
US 2011/0250119 A1    Oct. 13, 2011

(30) Foreign Application Priority Data
Dec. 18, 2008   (BR) .................................... 0805566

(51) Int. Cl.
*C10G 11/18*        (2006.01)
*C07C 273/04*      (2006.01)
(Continued)

(52) U.S. Cl.
CPC .............. *C10G 11/185* (2013.01); *C10G 11/18* (2013.01); *C01B 3/025* (2013.01); *C07C 273/10* (2013.01); *C01B 3/34* (2013.01); *C01C 1/0488* (2013.01); *C07C 4/06* (2013.01); *C07C 273/04* (2013.01); *C10G 11/05* (2013.01); *C10G 11/182* (2013.01); *C10G 70/041* (2013.01);
(Continued)

(58) Field of Classification Search
CPC ........ C10G 11/04; C10G 11/05; C10G 11/18; C10G 11/182; C10G 11/185; C01B 3/025; C07C 273/04; C07C 273/10
USPC .................... 208/100, 103, 113, 118, 120.01; 423/359; 564/67, 69
See application file for complete search history.

(56) References Cited

U.S. PATENT DOCUMENTS 3,862,899 A  *  1/1975  Murphy et al. .................. 208/93
4,617,182 A  *  10/1986  Brown et al. .................. 423/579
(Continued)

OTHER PUBLICATIONS

International Search Report of PCT/BR2009/000343 dated Dec. 15, 2009.

*Primary Examiner* — Renee E Robinson
(74) *Attorney, Agent, or Firm* — Sughrue Mion, PLLC

(57) ABSTRACT

An integrated process for the manufacture of olefins and intermediates for the production of ammonia and urea, comprising an FCC reactor, a regenerator, a steam reforming unit, an air-separation unit, an ammonia production unit and a urea production unit, is described. This process makes it possible to minimize $CO_2$ emissions to atmosphere, make use of heavy feedstocks of low added value (AR) for the production of light olefins, in addition to making maximum use of all the flows involved, thus increasing the energy efficiency achieved, all at the same time.

7 Claims, 1 Drawing Sheet

(51) Int. Cl.
*C07C 273/10* (2006.01)
*C01B 3/02* (2006.01)
*C01B 3/34* (2006.01)
*C01C 1/04* (2006.01)
*C07C 4/06* (2006.01)
*C10G 11/05* (2006.01)
*C10G 70/04* (2006.01)

(52) U.S. Cl.
CPC . *C10G 2300/4043* (2013.01); *C10G 2300/107* (2013.01); *C10G 2400/02* (2013.01); *C10G 2400/26* (2013.01); *C01B 2203/0205* (2013.01); *C01B 2203/0283* (2013.01); *C01B 2203/043* (2013.01); *C01B 2203/0475* (2013.01); *C01B 2203/063* (2013.01); *C01B 2203/068* (2013.01); *C07C 2529/08* (2013.01); *C07C 2529/40* (2013.01); *C10G 2400/20* (2013.01); *C10G 2300/301* (2013.01); *C10G 2300/708* (2013.01)

USPC ........ 208/120.01; 208/103; 423/359; 564/67; 564/69

(56) References Cited

U.S. PATENT DOCUMENTS

| | | |
|---|---|---|
| 4,690,812 A | 9/1987 | Ranke et al. |
| 5,506,365 A * | 4/1996 | Mauleon et al. .............. 585/329 |
| 5,565,089 A * | 10/1996 | Ramachandran et al. .... 208/113 |
| 6,616,899 B1 * | 9/2003 | Upson .......................... 422/139 |
| 2002/0195373 A1 * | 12/2002 | Ino et al. ....................... 208/113 |
| 2006/0116544 A1 | 6/2006 | Wakui et al. |
| 2008/0015105 A1 | 1/2008 | Lau et al. |
| 2008/0290000 A1 | 11/2008 | Towler |
| 2009/0032439 A1 | 2/2009 | Couch et al. |

* cited by examiner

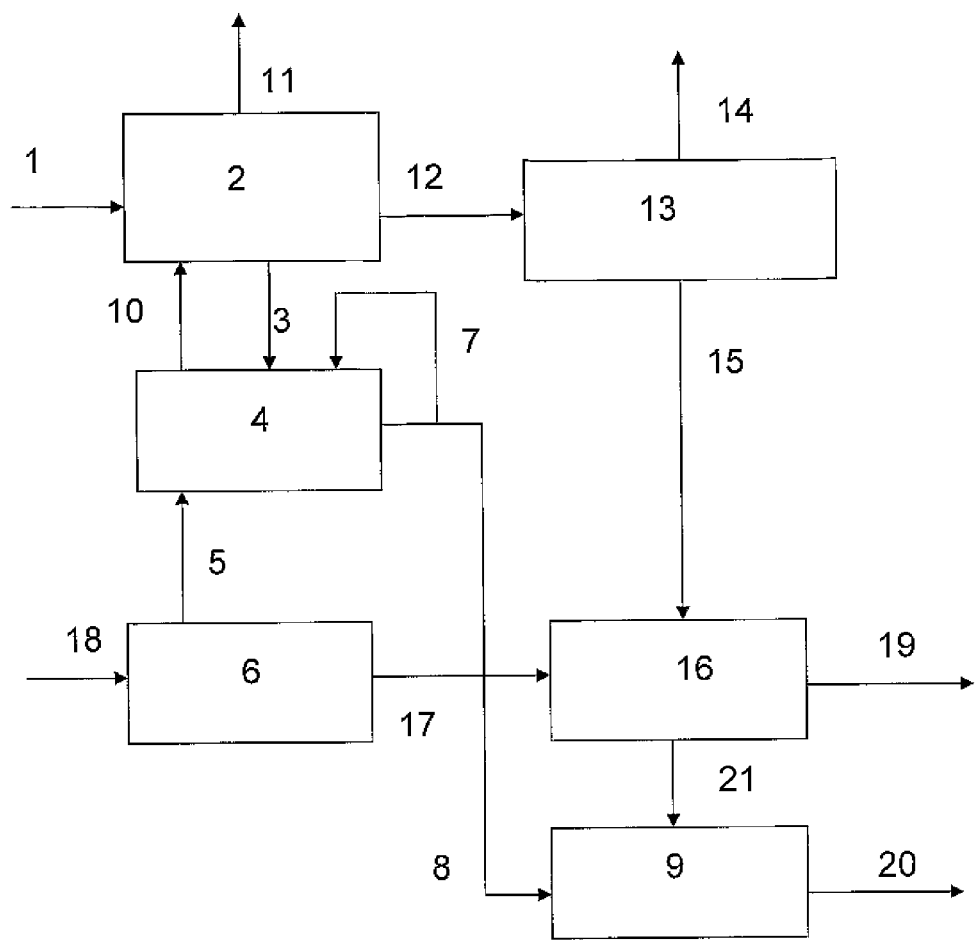

US 8,932,456 B2

INTEGRATED PROCESS FOR THE MANUFACTURE OF OLEFINS AND INTERMEDIATES FOR THE PRODUCTIONS OF AMMONIA AND UREA

CROSS REFERENCE TO RELATED APPLICATIONS

The present application is a National Stage entry of PCT/BR2009/000343 filed Oct. 21, 2009, and claims priority to Brazilian Application No. PI 0805566-1, filed Dec. 18, 2008, the contents of which are incorporated herein by reference in their entirety.

This invention relates to the field of integrated processes for the production of light olefins, ammonia and urea, with a view to improving their energy efficiency and reducing the quantity of emissions produced. More specifically the invention relates to integration of a fluid catalytic cracking process, preferably for the production of light olefins, with a process for the generation of hydrogen by steam reforming and an air-separation unit (ASU) to produce intermediates such as hydrogen ($H_2$), nitrogen ($N_2$) and carbon dioxide ($CO_2$) which will be used as feedstock for units for the production of nitrogen fertilizers such as ammonia ($NH_3$) and urea.

BASIS OF THE INVENTION

The increasing demand for fertilizers has been driven by a convergence of factors, including population growth, a fall in world reserves of grain and the increase in the production of biofuels, with world fertilizer consumption increasing by an average 25 of 31% between 1996 and 2008.

Most of this demand has been directed towards nitrogen fertilizers. These fertilizers have nitrogen in their compositions as a principal nutrient, and derive from the manufacture of anhydrous ammonia ($NH_3$), the starting material for all synthetic nitrogen compounds. Anhydrous ammonia is a gas obtained by the direct reaction of nitrogen from the atmosphere with hydrogen from various sources, such as for example natural gas and naphtha.

Natural gas is the main raw material for production of the hydrogen required for the production of ammonia. Approximately 90% of the world output of ammonia has natural gas as its primary source, and this would appear to be an essential factor for the viability of future projects for the production of nitrogen fertilizers.

The use of natural gas for the production of hydrogen for subsequent use in the manufacture of ammonia nevertheless has problems in connection with its availability and the volatility of its prices.

In addition to this, it is known that when natural gas is used as a raw material for the production of ammonia, ammonia and carbon dioxide are not produced in stoichiometric quantities for the subsequent synthesis of urea, with the result that excess ammonia is produced in relation to carbon dioxide ($CO_2$). Thus for all the ammonia to be consumed in the production of urea it is necessary to have an additional amount of carbon dioxide.

In general this amount is obtained by burning natural gas, to provide heat for the production of synthesis gas (a mixture of hydrogen, carbon dioxide and nitrogen obtained from steam reforming and/or autothermal reforming of a hydrocarbon, such as natural gas or naphtha).

For the carbon dioxide obtained from the burning of natural gas to be used in urea production units it has to be recovered, or separated, or absorbed, generally using aqueous solutions of amines.

These recovery processes have the disadvantage however that they involve a number of interdependent chemical reactions which are difficult to perform and control, as well as giving rise to wastes, such as oxidized amine in considerable quantities, which are difficult to dispose of.

One of the alternatives currently in use to overcome the problems linked with the use of natural gas as a source of hydrogen and carbon dioxide for the production of ammonia and urea respectively is hydrogen generation by the gasification of feedstocks such as coal, petroleum coke, and other wastes. In this case the hydrocarbon is gasified in the presence of pure oxygen, obtained after separating off nitrogen from the air in an air-separation unit (ASU).

The integration of gasification processes with natural gas plants to produce ammonia has not provided adequate energy efficiency. In particular there has not been sufficient steam generation to meet the process's demands.

Many studies to achieve greater energy efficiency and lower $CO_2$ emission in integrated processes for the production of fertilizers, more specifically ammonia and urea, are in progress.

U.S. Patent Application 2007/0245787 discloses a process for the production of ammonia and nitrogen fertilizers based on the partial oxidation of fossil fuel, with the co-production of polycarbonate and low $CO_2$ emissions. The fossil fuel reacts with the oxygen in the air and steam in an electrical discharge plasma, producing polycarbonate, hydrogen and nitrogen, which are subsequently separated, purified and used in the synthesis of ammonia.

U.S. Patent Application 2004/028595 has already described a method for the production of ammonia from a mixture of nitrogen and hydrogen obtained from the autothermal reforming of natural gas. The natural gas is fed to an autothermal reformer together with a flow rich in oxygen at temperatures of between 900° C. and 1200° C. and pressures of 40 to 100 bar in the presence of a reforming catalyst. The crude synthesis gas which leaves the reformer is cooled and passed to a shift reactor to convert CO to $H_2$ and thus bring about conversion into synthesis gas with a high $H_2$ content in a dry state. The synthesis gas is subsequently subjected to a purification process to remove $CO_2$, CO and $CH_4$, and thus produce an $N_2$—$H_2$ mixture which is used for the synthesis of ammonia.

U.S. Pat. No. 6,586,480 discloses an integrated process for the production of liquid hydrocarbons and ammonia. In this case a flow of synthesis gas obtained from the reforming of natural gas with steam and a mixture containing oxygen passes through a Fischer-Tropech process producing liquid hydrocarbons, carbon dioxide, nitrogen and hydrogen. After separation the flows of nitrogen and hydrogen are delivered to the ammonia production process. In this case it is not necessary to use a shift unit to convert the CO to $H_2$ as in conventional processes because the CO reacts with some of the $H_2$ in the Fischer-Tropsch reactor to produce liquid hydrocarbons.

U.S. Pat. No. 6,723,876 has already described an integrated process for the production of ammonia and urea. In this document the ammonia produced from synthesis gas reacts with carbon dioxide to produce ammonium carbamate, which is decomposed yielding urea.

Nevertheless there is no description or suggestion in the literature of an integrated process for the production of light olefins and intermediates for the production of ammonia and urea which makes maximum use of all the flows involved, thus increasing the energy efficiency achieved.

SUMMARY OF THE INVENTION

This invention relates to a process incorporating a fluid catalytic cracking unit, preferably for the production of light olefins, more specifically ethene and propene, a unit for the production of hydrogen by steam reforming and an air-separation unit so that the flows produced are used in processes for the synthesis of ammonia and urea.

More specifically, the scope of the invention relates to an integrated process which includes a fluid catalytic cracking unit, preferably adjusted to operate under conditions to maximize the production of light olefins such as, but not limited to, ethene and propene, in which the unit uses an oxygen-rich flow mixed with an inert, the inert preferably $CO_2$, to regenerate coke deposited on the surface of the cracking catalyst, the oxygen used being generated in an air-separation unit which in turn generates as a by-product a flow of pure nitrogen, in which use of an oxygen-rich flow mixed with an inert gas, preferably $CO_2$, for burning off the coke produced on the surface of the catalyst, provides a flow rich in $CO_2$ leaving the regenerator, as is not the case with a conventional fluid catalytic cracking unit.

Also within the scope of the invention the integrated process includes a steam reforming unit in which the unit uses a flow of hydrocarbons originating from the fluid catalytic cracking unit as a feedstock, this flow preferably comprising hydrogen and hydrocarbons in the C1 to C2 range (fuel gas) and/or C3 to C4 range (liquefied petroleum gas) and/or hydrocarbons having five or more carbon atoms with a boiling range below 220° C. (naphtha), while the mixture originating from the reforming unit, basically comprising $CO_2$, CO and $H_2$, can be delivered to a shift reactor to convert the CO to $H_2$ by reacting the CO with steam in the presence of a catalyst, the resulting mixture of $CO_2$ and $H_2$ being suitable for delivery to a $CO_2$ and $H_2$ separation unit, such as a PSA unit, to obtain a flow of pure $H_2$. Also within the scope of the invention the integrated process includes using a flow of pure $H_2$ generated in the reforming unit and shift reactor which is delivered to an ammonia production unit together with the flow of pure $N_2$ produced in the air-separation unit, while the ammonia produced can be delivered to a reactor for the production of urea together with a flow rich in $CO_2$ produced in the regenerator of the fluid catalytic cracking unit.

The invention makes it possible to reduce carbon dioxide emission because the $CO_2$ produced during the stage of regenerating the FCC catalyst is made use of in the synthesis of urea.

Contrary to what happens in conventional steam reforming units used for the synthesis of nitrogen fertilizers, where air is used in addition to steam for the partial oxidation of a feedstock comprising methane originating from natural gas and also as a source of nitrogen, in this invention the feedstock for the steam reforming unit comprises hydrocarbons of greater molecular mass (fuel gas, LPG and/or naphtha), the reforming being only carried out with steam. As only steam is used to carry out the reforming, there is no longer any need to use large-scale equipment designed for the use of air.

The invention also makes it possible to achieve greater energy efficiency through using a single source of air as a source of oxygen and nitrogen for both regenerating cracking catalyst and producing nitrogenated fertilizers.

This being the case, this invention makes it possible to reduce $CO_2$ emissions to the atmosphere and make use of heavy feedstocks of low added value in the production of light olefins at the same time, in addition to making maximum use of all the flows involved, thus increasing the energy efficiency achieved.

BRIEF DESCRIPTION OF THE DRAWINGS

FIG. 1 illustrates a flow diagram of the process in this invention in a simplified way.

DETAILED DESCRIPTION OF THE INVENTION

Overall, this invention relates to a process which integrates the production of light olefins by fluid catalytic cracking with the production of intermediates for the synthesis of ammonia and urea.

In this process the fluid catalytic cracking unit (FCC), which comprises an FCC reactor and a regenerator together with an air-separation unit and a steam reforming unit produces intermediates, in this particular case hydrogen, nitrogen and carbon dioxide, for the production of ammonia and urea, products which are useful as fertilizers.

Thus the integrated process for the production of light olefins and intermediates for the production of ammonia and urea according to this invention comprises the following stages:
(a) feeding a feedstock comprising a flow of hydrocarbons from petroleum refining having an initial boiling point above 250° C. in an FCC converter to provide contact between the feedstock and a catalyst containing alumina, preferably between 20% and 50% by mass, and zeolite, preferably between 20% and 45% by mass, the zeolite being preferably Y, USY, RE-Y, RE-USY and/or ZSM-5, in which RE indicates rare earths, in a concentration of between 0.5% to 5% by mass, which may also contain between 5% and 30% of silica and kaolin, operating at temperatures in the range from 500° C. to 700° C. and pressures in the range from 0.10 MPa to 0.45 MPa,
(b) separating the products from hydrocarbons and deactivated catalyst on leaving the reactor,
(c) delivering the deactivated catalyst to a steam rectification area, from there to a regenerator and burning off the coke deposited on the catalyst particles with a mixture of $O_2$ and an inert gas, preferably $CO_2$ in a proportion of 15% to 35% by mass of $O_2$, preferably between 20% and 30%, where the $O_2$ originates from an air-separation unit,
(d) delivering the flow of $N_2$ obtained from the airseparation unit to an ammonia production unit,
(e) recovering the flow of $CO_2$ produced in the FCC regenerator, with the possibility of this $CO_2$ flow being recycled to the regenerator in a proportion of 70% to 90%, preferably 75% to 85%, and delivering the rest of the flow to a urea production unit,
(f) recovering the flow of hydrocarbons obtained in the FCC reactor and separating them into other flows according to the boiling points of the hydrocarbons, the first comprising hydrogen and hydrocarbons in the range from between C1 to C2 (fuel gas), the second comprising hydrocarbons in the range from C3 to C4 (LPG) and the third comprising hydrocarbons with 5 or more carbon atoms and a boiling point below 220° C. (naphtha), and other flows in accordance with the conventional FCC process,
(g) recovering the fraction corresponding to ethene from the flow comprising the fuel gas and the fraction corresponding to propene from the flow comprising LPG, the ethene and the propene being the end products,
(h) delivering the flows of fuel gas without ethene and LPG without propene and/or naphtha obtained from the FCC to a hydrogen generating unit comprising a steam reforming unit, optionally a CO shift reactor and a hydrogen separation unit,
(i) delivering the flow of hydrogen obtained from the hydrogen generating unit to a unit for the production of ammonia,
(j) optionally delivering the flow of carbon dioxide obtained from the hydrogen generating unit to a urea production unit.

The diagram shown in appended FIG. 1 illustrates the flow in the process according to the invention in a simplified way, including an FCC reactor, a regenerator, an air-separation unit, a hydrogen generation unit, a unit for the production of ammonia, and a unit for the production of urea, in which: an atmospheric residue (AR) feedstock (1) comprising hydrocarbons having an initial boiling point above 250° C. is fed to a fluid catalytic cracking (FCC) reactor (2) using a catalyst containing alumina, preferably between 20% and 50% by weight, and zeolite, preferably between 20% and 45% by weight, the zeolite preferably being Y, USY, RE-Y, RE-USY and/or ZSM-5, in which RE indicates rare earths, in a concentration of between 0.5% and 5% by weight, which may also contain between 5% and 30% of silica and kaolin, preferably operating under conditions such that light olefins are maximized, at temperatures within the range from 500° C. to 700° C., preferably between 550° C. and 650° C. and more preferably between 580° C. and 620° C. and pressures in the range from 0.10 MPa to 0.45 MPa.

On leaving the FCC reactor after the cracking reactions a deactivated catalyst (3) is separated from the reaction products.

The deactivated catalyst (3) then passes through a stage of regeneration by oxycombustion. A flow of pure oxygen (5) separated from a flow of air (18) in an air-separation unit (6) is used to burn the coke deposited on the deactivated catalyst in a regenerator (4).

The use of oxycombustion, together with the use of a flow of recycled $CO_2$ (7), makes it possible to effectively increase the concentration of $CO_2$ in the combustion gases up to 98%, which results in easier recovery and makes it possible for this flow rich in $CO_2$ (8) to be used in a urea production unit (9).

The regenerated catalyst (10) returns to the FCC reactor at a high temperature sufficient to provide heat for the endothermic reactions in the process.

The flows of hydrocarbons recovered in the FCC process comprise: fuel gas, LPG, light olefins (C2= and C3=), naphtha ($C_5$+–220° C.), and other hydrocarbons (>220° C.). These flows are separated, with the recovery of a first flow comprising ethene and propene (11) and a second flow which may include fuel gas, LPG and/or naphtha (12).

The flow comprising fuel gas, LPG and/or naphtha (12) is delivered to a hydrogen generating unit (13) giving rise to two flows, one of $CO_2$ (14), which is optionally delivered to the urea production unit, and a flow of hydrogen (15) which is delivered to an ammonia production unit (16).

The ammonia production unit (16) also receives a flow of nitrogen (17) from the air-separation unit (6) as a feedstock. The ammonia ($NH_3$) produced in the ammonia production unit can be delivered to the urea production unit via flow (21).

The flow comprising ethene and propene (11) is subsequently made use of for the production of basic petrochemicals. The flows of ammonia (19) and urea (20) can be recovered as an end product or used as a feedstock for other fertilizer production processes.

The invention claimed is:
1. An integrated process for production of light olefins and intermediates for production of ammonia and urea, comprising:
(a) feeding a feedstock of hydrocarbons from petroleum refining to an FCC converter to place the feedstock in contact with a catalyst containing alumina and zeolite in a fluidized bed reactor in order to obtain a flow of light hydrocarbons,
(b) separating the light hydrocarbon products and deactivated catalyst on leaving the reactor,
(c) delivering the deactivated catalyst to a rectification zone, from there to a regenerator and burning off coke deposited on the catalyst with a mixture of $O_2$ and inert gas in a proportion of 15% to 35% by mass of $O_2$, where the $O_2$ comes from an air-separation unit,
(d) delivering a flow of $N_2$ obtained from the air-separation unit to a unit for the production of ammonia,
(e) recovering a flow of $CO_2$ produced in the regenerator, recycling 70% to 90% to the regenerator and delivering the remainder of the flow to a urea production unit,
(f) recovering the flow of light hydrocarbons obtained in the FCC reactor and separating it into other flows, including a first flow comprising hydrogen and hydrocarbons in the range from C1 to C2 (fuel gas), a second flow comprising hydrocarbons in the range from C3 to C4 (LPG) and a third flow comprising hydrocarbons with 5 or more carbon atoms having a boiling point below 220° C. (naphtha),
(g) recovering a fraction corresponding to ethene from the flow comprising fuel gas and a fraction corresponding to propene from the flow comprising LPG, the ethene and the propene being the end products,
(h) delivering the flows of fuel gas without ethene and LPG without propene and/or naphtha obtained in the FCC to a unit for the generation of hydrogen which comprises a steam reforming unit to obtain a flow of hydrogen and another of $CO_2$,
(i) delivering the flow of hydrogen obtained in the hydrogen generating unit to an ammonia production unit, and
(j) delivering the flow of carbon dioxide obtained in the steam reforming unit to a urea production unit.

2. The integrated process for the production of light olefins and intermediates for the production of ammonia and urea according to claim 1, characterized in that the fluidized bed reactor operates at temperatures in the range from 500° C. to 700° C. and at pressures in the range from 0.10 MPa to 0.45 MPa.

3. The integrated process for the production of light olefins and intermediates for the production of ammonia and urea according to claim 1, characterized in that the feedstock to the FCC reactor comprises a flow of hydrocarbons from petroleum refining having an initial boiling point of over 250° C. (AR).

4. The integrated process for the production of light olefins and intermediates for the production of ammonia and urea according to claim 1, characterized in that the catalyst in contact with the feedstock of hydrocarbons from petroleum refining comprises alumina in a concentration from 20% to 50% by mass and zeolite in a concentration from 20% to 45% by mass.

5. The integrated process for the production of light olefins and intermediates for the production of ammonia and urea according to claim 4, characterized in that the zeolite present in the catalyst in contact with the feedstock of hydrocarbons from petroleum refining is selected from the group consisting of Y, USY, RE-Y, RE-USY and ZSM-5.

6. The integrated process for the production of light olefins and intermediates for the production of ammonia and urea according to claim 5, characterized in that the rare earths (RE) content of the RE-Y and RE-USY zeolites is from 0.5% to 5% by mass.

7. The integrated process for the production of light olefins and intermediates for the production of ammonia and urea according to claim 4, characterized in that the catalyst in contact with the feedstock of hydrocarbons from petroleum refining further comprises from 5% to 30% of silica by mass and kaolin.

* * * * *